United States Patent [19]

Chen et al.

[11] 4,321,327

[45] Mar. 23, 1982

[54] PREPARATION OF SPHERICAL SHAPED MYCELIAL PELLETS

[75] Inventors: Li F. Chen; Cheng S. Gong; George T. Tsao, all of West Lafayette, Ind.

[73] Assignee: Purdue Research Foundation, West Lafayette, Ind.

[21] Appl. No.: 100,816

[22] Filed: Dec. 6, 1979

[51] Int. Cl.³ .................. C12P 7/06; C12P 1/02; C12N 11/02; C12N 11/12

[52] U.S. Cl. .................. 435/161; 435/171; 435/174; 435/177; 435/179; 435/254; 435/288

[58] Field of Search .......... 435/174, 176, 177, 178, 435/179, 180, 182, 253, 254, 161, 170, 171, 288

[56] References Cited

U.S. PATENT DOCUMENTS 4,090,022 5/1978 Tsao et al. .................. 435/179 X
4,208,482 6/1980 Ehrenthal et al. .................. 435/178

OTHER PUBLICATIONS

Atkinson et al., The Completely Mixed Microbial Film Fermenter, Trans. Instn. Chem. Engrs., vol. 50, 1972, pp. 208-216.

Jack, T. R., The Immobilization of Whole Cells, Advances in Biochem. Eng., vol. 5, 1977, pp. 128-135 & 140-141.

Primary Examiner—David M. Naff
Attorney, Agent, or Firm—Cushman, Darby & Cushman

[57] ABSTRACT

Spherical shaped mycelial pellets having a support core and which are suitable for biocatalytic conversion of organic compounds are produced by dissolving a cellulose derivative in a solvent to form a solution, mixing spores of a mycelial microorganism with the solution, precipitating the cellulose derivative to form porous beads containing the spores, and incubating the beads in a culture medium. Alternatively, the pellets may be produced by dissolving agar in water, mixing the agar solution with spores of a mycelial microorganism, precipitating the agar to form beads containing the spores and incubating the beads in a culture medium.

28 Claims, No Drawings

PREPARATION OF SPHERICAL SHAPED MYCELIAL PELLETS

BACKGROUND OF THE INVENTION

The invention relates generally to the art of biological catalytic reactor systems with mycelia of microorganisms, especially mycelial fungi, and more particularly to mycelial pellets having a support core and use thereof for biocatalytic conversions, as well as the preparation of the biologically active mycelial pellets.

Microorganisms have long been employed in the biocatalytic conversion of organic compounds. Exemplary of such conversions, to mention but a few, include conversion of simple sugars to useful products such as alcohols and organic acids; production of enzymes; synthesis of antibiotics and isomerization of sugars. Thus, the conversion of various sugars has to some degree involved the use of fungi, but such use has been generally limited to an unsupported vegetative mass. U.S. Pat. No. 4,127,447 describes a biocatalytic reaction involving a packed column packed with a support material to which have been attached the needed anaerobic microorganisms. U.S. Pat. No. 4,090,022, describes the use of porous cellulose beads to which active biological agents (e.g. enzymes) may be attached by means of chemical bonding. In each case the active agent is bonded to the support, thus necessitating preparation of the support for attachment of the desired agent.

The use of mycelial fungi in biocatalytic systems has been limited due to the difficulty in handling such masses. While supported mycelia would be desirable, no satisfactory method has been developed prior to the present invention, and methods to date require preparation of the support surface in order to attach the active agent. It is known that some mycelial fungi can form mycelial pellets in a conventional shaking culture. While such a pellet form is more desirable than the unshaped vegetative mass, the pellets suffer a number of disadvantages. For example, if placed in a column reactor, under flow pressure, the pellet may collapse and plugging will occur. Furthermore, handling and recovery of these pellets are hampered due to the weak physical properties of the pellets.

Since the discovery of the present invention, K. Gbewonyo and D. I. C. Wang have reported the growth of mycelial microorganisms on spherical diatomaceous beads (Abstract of Papers presented at 178th ACS Meeting, Washington, D.C., Sept. 10–13, 1979—American Chemical Society Division of Microbial and Biochemical Technology). The report describes the growth of *Penicillium chrysogenum* on porous celite beads resulting in the projection of hyphae outwards from the bead surface. No surface layer of structural integrity is reported.

In accordance with the present invention, we have discovered useful spherical shaped mycelial pellets which possess an inner rigid structural core which is surrounded by a porous webbed layer having structural integrity of a mycelial microorganism. The porous webbed layer thus forms a spherical encasement of structural integrity about the rigid core.

Accordingly, it is the primary object of the present invention to provide mycelial pellets having a core support surrounded by a porous webbed layer of structural integrity of a mycelial microorganism.

It is a further object of the present invention to provide an improved means for carrying out the biocatalytic conversions of organic compounds.

These and other objects of the present invention will become more apparent from the discussion which follows.

SUMMARY OF THE INVENTION

When mycelial microorganisms, such as fungi, grow in a liquid medium, their mycelia form a loose cotton-like mass. As used herein, mycelial microorganisms are defined as those living microorganisms, the vegetative portion of which forms filamentous hyphae. Such mycelial microorganisms include various fungi (including some yeasts), bacteria (e.g., Actinomyces) and algae such as blue-green algae. Of particular interest are mycelial fungi, especially from the genus Rhizopus and Mucor.

Some mycelial fungi can form pellets when they are grown in a circular action shaking incubator. The formation of pellet increases the cell density and facilitates the separation of the cell mass from the liquid products. Unfortunately not every fungus is able to form such mycelial pellets in a circular action shaking incubator. It is desirable to prepare the mycelia in a pellet form for use in a fermentation process, especially in a continuous fermentation process. In a continuous fermentation process, the flow properties and the cell density determine the efficiency of the fermentation process. The fungal mycelial pellets prepared by conventional circular action shaking cultures are loose and fragile when they are packed in a column reactor. They are easily deformed under small pressure which may result from a flow of the reaction substrate.

The present invention also provides a method for the preparation of mycelial microorganism pellets from all types of mycelial microorganisms, particularly fungi, with a rigid physical support core. Those fungi which are incapable of forming mycelial pellets in conventional shaking cultures can form mycelial pellets by the present method.

The pellets thus prepared may if desired possess a rigid physical support core, and thus exhibit good flow properties when they are used in a continuous fermentation reactor. The diffusion of the nutrients and the products into and out of the conventional mycelial pellets is rather slow. The supported mycelial pellets prepared by the present invention grow into round pellets with a porous webbed layer of mycelia generally having a thickness of from about 0.1 mm to about 5 mm (preferably 1 to 3 mm), the webbed layer thereby forming a spherical encasement of structural integrity about the rigid core. The distance between the support core and the mycelial layer will vary from 0 to 1 cm (preferably about 5 mm) depending upon the initial spore concentration and incubation time. The pellets with such structural mycelial layers allow easy diffusion of nutrients into and passage of products out of the pellets.

The mycelial pellets prepared according to the present invention possess an outer mycelial layer having a highly texturized structure which is resistant to shear force. Mycelial pellets prepared by conventional method have loose mycelial structure that would be sheared off at high flow rates experienced in a continuous reactor. The mycelial pellets made according to this invention can be regenerated even at a high flow rate in the reactor because the "seed" spores still exist inside the bead core.

One embodiment of the present invention relating to the preparation of mycelial pellets is in part based on the procedure of making cellulose beads as described in U.S. Pat. No. 4,090,022 (the entire contents of which is incorporated herein by reference). The procedure is as follows:

(a) Dissolving a hydrolyzable cellulose derivative in an inert organic, water-miscible solvent to form a solution having a density greater than that of a precipitation solution;

(b) Mix mycelial microorganisms spores (e.g. fungal spores) with the cellulose derivative solution;

(c) Distribute the solution in the form of droplets into a precipitation solution or cool air to form porous beads containing said spores;

(d) Separating the precipitated beads from the precipitation solution if used;

(e) Eliminate undesirable bacteria by chemical sterilization or washing with sterilized water thoroughly;

(f) If cellulose beads are desired, the beads can be regenerated before incubation of the beads;

(g) Incubate the beads containing the spores in a liquid culture medium with agitation (e.g. in a circular action shaking incubator).

Thus, the process for the preparation of biologically active mycelial pellets having a physical support generally comprising the steps of:

(a) dissolving a hydrolyzable cellulose derivative in an inert organic, water-miscible solvent to form a solution having a density greater than that of a precipitation solution;

(b) mixing mycelial microorganism spores with said solution and distributing the resulting solution in the form of droplets into a precipitation solution or cool air whereby said cellulose derivative is precipitated in the form of uniformly porous beads, said beads containing said spores;

(c) separating the precipitated beads from said precipitation solution if used;

(d) washing the separated porous beads to eliminate undesirable bacteria and facilitate incubation of said spores;

(e) incubating said separated porous beads in a liquid culture medium for a period of time sufficient to produce a round pellet characterized by a rigid porous bead core surrounded by a porous webbed layer having structural integrity of a mycelial microorganism, depending upon the initial spore concentration and length of incubation, the space between the core and layer may be substantially void, with a number of mycelia forming a filamentous connection between the core and webbed layer.

The inert organic water miscible solvent may be a single liquid or combination of liquids as described in the aforementioned U.S. Pat. No. 4,090,022 as well as its predecessor, U.S. Pat. No. 4,063,017, the entire contents of which are also incorporated herein by reference.

As used herein, the term "precipitation solution" is defined as a liquid solution which is a non-solvent for the cellulose derivative and is miscible with the above inert organic, water-miscible solvent. By means of illustration, the precipitation solution may be water or an aqueous solution. The precipitation solution is therefore miscible with solvent components. Thus, it will be appreciated that when one dissolves the cellulose derivative in the organic solvent and subsequently adds a drop of the resulting solvent solution to the precipitation solution, the cellulose derivative will coagulate and precipitate out due to the phase inversion which the cellulose derivative undergoes thereby forming the desired porous cellulose bead.

When employing an aqueous precipitation solution, one may suitable use as solvent component (a) a member from the group consisting of acetone, formamide a mixture of acetone and methanol, methyl acetate, a mixture of methylene dichloride and methanol, methyl ethyl ketone and dimethyl sulfoxide. The solvent component (b) may thus be suitably chosen from a member selected from the group consisting of dimethyl sulfoxide, formamide, methyl acetate, cyclohexanone, methylene dichloride, ethylene dichloride, a mixture of methylene dichloride and methanol and a mixture of ethylene dichloride and methanol.

The preferred precipitation solution into which the solution of cellulose derivative is to be distributed generally consists of water, but may be an aqueous solution which contains suitable amounts of non-ionic or ionic surfactants to reduce the surface tension thereof and facilitate formation of the porous beads.

Alternatively, one may prepare the supported pellets by the steps:

(a) Providing a porous core support (e.g. prepare cellulose or cellulose derivative beads);

(b) Absorb the fungal spores with these beads; and (c) Incubating the beads with agitation (e.g. in a circular action shaking incubator).

The physical and mechanical properties of the mycelial pellets can be improved by cross-linking the mycelium or impregnating the mycelial pellet with cellulose or cellulose derivatives or other inexpensive polymers. Suitable cross-linking agents which could be used include among others glutaraldehyde and diisocyanate.

One may also prepare biologically active mycelial pellets with agar, in accordance with a further embodiment of the present invention. Agar is a carbohydrate and its solution melts at 90° C., solidifying at about 45° C. Because it is inert to most microorganisms, agar is used to solidify liquid culture media. These characteristics of agar can be utilized as a supporting core material to trap spores of mycelial microorganisms and produce mycelial pellets.

In general agar may be used as a supporting material in preparing mycelial pellets by:

(a) dissolving agar in hot water to form an agar solution;

(b) cooling the agar solution to a temperature of greater than 45° C., but below the temperature at which the spores added in step (c) would be killed (generally from between about 45° and 80° C. preferably about 50° C.);

(c) mixing the agar solution of step (b) with spores of a mycelial microorganism and dispersing the resulting mixture in the form of droplets into cool air or an aqueous precipitation solution at a temperature below 45° C. whereby said agar is precipitated in the form of uniform beads containing said spores;

(d) separating the agar beads from the precipitation solution if used, or alternatively, one may employ the same solution for both precipitation and incubation; and (e) incubating the agar beads with agitation (e.g. in a circular action shaking incubator) for a period of time sufficient to produce a round pellet characterized by a rigid round agar core surrounded by porous webbed layer of mycelial having structural integrity of a microorganism.

Incubation of the mycelial spores according to the present invention is carried out with agitation using nutrients, pH and temperature parameters which are conventional for the microorganisms employed. Generally, the nutrient medium is an aqueous solution containing a source of the essential elements (i.e. carbon and nitrogen) to support the vegetative growth of the microorganism hyphae. Generally glucose and ammonia may be employed in the nutrient medium. The pH of the medium may vary generally from about 3 to 8, but preferably ranges from about 4.5 to 6.5. The temperature for incubation may also vary widely depending on the microorganism (e.g. 0° to 70° C., preferably about 20° to 38° C.).

The amount of spores to be added to the core forming medium is not critical, but should be at a level sufficient to provide at least one spore for each bead core produced or impregnated. Generally, a concentration of at least about $10^6$ spore per 100 ml of core forming medium is sufficient to provide an optimum level of germination.

The mycelial pellets of the present invention may be further characterized as having a substantially void space between the core surface and the webbed mycelial layer depending upon initial spore concentration and incubation time. The space may be as great as 1 cm when measured from the core surface to the webbed layer depending upon the number of spores present in the bead core and time of incubation. By referring to a substantially void space, it is to be understood that some of the hyphae resulting from the vegetative growth of the spores may remain anchored to the spore thereby forming a network of filamentous connections between the bead core and webbed mycelial layer encompassing the core.

The following materials and procedures were employed in evaluating the present invention.

ISOLATION AND MAINTENANCE OF THE MUCORACEOUS FUNGI

Several Chinese yeast preparations were obtained from various locations on the island of Taiwan. The dry circular cake of Chinese yeast cultures was first cracked and broken into a fine powder. This powder was suspended in sterile water and plated onto potato dextrose agar (PDA) plates containing 0.02% rose-bengal (Sigma). Rose-bengal inhibits the growth of yeasts and bacteria, but it inhibits the growth of fast-growing molds to a lesser extent. The PDA rose-bengal plates were incubated at 30° C. for 48 hours before the mycelial edge of a fungal colony was transferred. Single sporangiospores were then isolated. Several isolates were identified as Rhizopus species, and the rest were identified as Mucor species.

Cultures were maintained at 4° C. on PDA slants and transferred monthly.

Inoculum and Cultural Conditions

Both growing and non-growing mycelial systems were used. The growing mycelial system was as follows Small amounts of sporangiospore suspension were inoculated into 250 ml. Erlenmeyer flasks containing 100 ml of basic salts medium (BSM) consisting of 2.0 gm. $KH_2PO_4$, 1.4 gm $(NH_4)_2SO_4$, 0.3 gm. urea, 0.3 gm $CaCl_2$, 0.3 gm. $MgSO_4.7H_2O$, 1.0 gm. peptone (Difco), 10.0 gm. either glucose or xylose, 1.0 mg. $Fe^{++}$, 0.5 mg. $Mn^{++}$, 0.8 mg. $Zn^{++}$, and 0.5 mg. $Co^{++}$, each per liter of culture medium, and finally 0.011 M in sodium citrate buffer, pH 5.8. These cultures were incubated at 30° C. overnight on a reciprocal shaker and then harvested by filtration.

The non-growing mycelial system was as follows

Fresh mycelia, harvested from the growing mycelial system, were introduced into a 250 ml. Erlenmeyer flask containing 100 ml. of BSM with either 20.0 gm. glucose, or 10 gm. xylose per 100 ml., and incubated at 30° C. in a New Brunswick psycrotherm incubator shaker. These cultures were kept under nitrogen gas for the appropriate period of time. Unless otherwise indicated, sugars and BSM broth were autoclaved separately and mixed before inoculation.

Determination of Dry Weight of Mycelia

Cultures were passed through lint-free Miracloth filters (Chicopee Mills, Inc.), the retained mycelia washed with distilled water, squeezed dry and allowed to dry in an 80° C. oven overnight.

The following examples are offered in order to more fully describe the invention, but are not to be construed as limiting the scope thereof.

EXAMPLE 1

Five grams of cellulose acetate were dissolved in 40 ml of solvent (6 parts acetone and 4 parts dimethyl sulfoxide) to form a 10% (W/v) solution. Spores of Rizopus spp. 0.1 gm were mixed into the cellulose acetate evenly. With a hand-made spray gun the cellulose solution was then sprayed into a water tank. The cellulose acetate beads coagulated in the water tank and precipitated to the bottom of the tank. The beads were collected and washed with tap water and then washed with sterilized water thoroughly. The washed beads were then incubated in a selective liquid medium in a circular action shaking incubator. After three days the mycelial pellets were formed.

EXAMPLE 2

After the beads were formed and collected as in Example 1, the spore containing cellulose acetate beads were regenerated to cellulose beads in a NaOH solution (1 N) for one hour and then washed thoroughly with sterilized water. After incubation for three days in the circular action shaking incubator, the mycelial pellets were formed.

EXAMPLE 3

The procedures of Examples 1 and 2 were repeated except that the fungal spores were from *Aspergillus niger*. Mycelial pellets having a rigid core encompassed by a porous layer of *A. niger* of structural integrity wwere obtained as in the foregoing examples.

EXAMPLE 4

Beads of cellulose acetate and cellulose were prepared, and thereafter the fungal spores were added to the beads. After stirring and washing some spores were absorbed in the beads. Incubation of both types of beads resulted in the formation of mycelial pellets having the structure of the present invention, although the porous webbed mycelial layer was looser than the resulting mycelial layer in Examples 1 to 3.

EXAMPLE 5

1 gm of agar was dissolved in 50 ml of water in a boiling water bath. The agar solution was cooled to 50° C. 50 mg of spores from Mucor sp was added to the solution and mixed. The solution was sprayed into a cold water tank (15° C.). Upon contacting the surface of the water, the agar solidified as droplets and sank to the bottom. After the spore containing agar beads were collected and washed thoroughly with sterilized water, the beads were incubated in a liquid medium in a circular-action shaking incubator for 3 days and the mycelial pellets were formed.

EXAMPLE 6

The beads containing spores from Rizopus spp. were prepared as in Example 5. Mycelial pellets were formed.

EXAMPLE 7

The spores of Rizopus spp. were mixed with agar beads prepared as in Example 5 except that spores were not added to the agar solution. After washing, a small quantity of spores were absorbed on the surface of the agar beads. The beads were incubated in a liquid medium in a circular action shaking incubator, and the mycelial pellets formed in three days. However, the structure of the mycelial wall of the pellets was looser than that in Examples 5 and 6.

The mycelial pellets of the present invention lend themselves to a wide variety of applications for the biocatalytic conversion of organic compounds. Thus, depending upon the conversion desired and selection of mycelial microorganism, one may carry out such conversions as:

(a) production of alcohols and/or organic acids from sugars;
(b) production of specific enzymes;
(c) synthesis of antibiotics (e.g. pencillin); and
(d) isomerization of organic compounds (e.g. sugars).

The mycelial pellets of the present invention are particularly well suited for use in column reactors as they provide enhanced flow and mass transfer properties over columns of packed mycelia or unsupported mycelial pellets. The mycelial pellets could also be used to provide a column reactor containing the pellets and which is suitable for use in home brewing operations.

Such a column containing mycelia capable of fermenting sugar solutions to alcohol could be stored at low temperatures (or alternatively the mycelial pellets could be freeze dried) which when used is merely connected to a sugar solution (e.g. grape juice or cider) for preparation of an alcoholic drink.

The invention, in its broadest aspects, is not limited to the specific details shown and described, but departures may be made from such details within the scope of the accompanying claims without departing from the principles of the invention. Furthermore, the invention may comprise, consist, or consist essentially, of the hereinbefore recited materials and steps.

What is claimed is:

1. A process for the preparation of biologically active mycelial pellets having a physical support core which comprises the steps of:
    (a) dissolving a hydrolyzable cellulose derivative on an inert organic, water-miscible solvent to form a solution having a density greater than that of a precipitation solution;
    (b) mixing spores of a mycelial microorganism with said solution and distributing the resulting solution in the form of droplets into a precipitation solution or cool air whereby said cellulose derivative is precipitated in the form of uniformly porous beads, said beads containing said spores;
    (c) separating the precipitated beads from said precipitation solution if used;
    (d) incubating the precipitated porous beads in an aqueous culture medium for a period of time sufficient to produce a round pellet characterized by a rigid spherical porous bead core surrounded by a porous integral webbed layer, said layer forming a spherical encasement of structural integrity about the rigid core and being composed of filamentous hyphae of a mycelial microorganism.

2. A process according to claim 1, wherein said cellulose derivative is selected from the group consisting of cellulose acetate, cellulose triacetate, and cellulose nitrate.

3. A process according to claim 1 wherein said microorganism is a fungi selected from the genus Rhizopus or Mucor.

4. A process according to claim 1 wherein the precipitated porous beads are washed with sterile water prior to incubating.

5. A process according to claim 4 wherein the incubation is carried out with agitation.

6. A process according to claim 1 wherein the distributing is accomplished by spraying.

7. A process according to claim 1 wherein said precipitation solution is selected from the group consisting of water, hexane, cyclohexane, octane, benzene and mixtures of water and ethanol or methanol.

8. A process according to claim 7 wherein said precipitation solution is water.

9. A process according to claim 1 wherein said solvent is a mixture of:
    (a) a member from the group consisting of acetone, a mixture of acetone and methanol or ethanol, methyl acetate, a mixture of methylene dichloride and methanol, methyl ethyl ketone, formamide and dimethyl sulfoxide; and
    (b) a member from the group consisting of dimethyl sulfoxide, formamide, methyl acetate, cyclohexanone, methylene dicholoride, ethylene dichloride, a mixture of methylene dicholoride and methanol, and a mixture of ethylene dicholoride and methanol.

10. A process according to claim 9 wherein said solvent is dimethyl sulfoxide, formamide or methyl acetate.

11. A process for the preparation of biologically active mycelial microorganism pellets which comprise the steps of:
    (a) dissolving agar in hot water to form an agar solution;
    (b) cooling the agar solution to a temperature of greater than 45° C. but below the temperature at which the spores added in step (c) would be killed;
    (c) mixing the agar solution of step (b) with spores of a mycelial microorganism and dispersing the resulting mixture in the form of droplets into cool air or an aqueous precipitation solution at a temperature below 45° C. whereby said agar is precipitated in the form of uniform beads containing said spores;
    (d) incubating the agar beads in an aqueous culture medium for a period of time sufficient to produce a round pellet characterized by a rigid round agar core surrounded by a porous integral webbed layer, said layer forming a spherical encasement of structural integrity about the rigid core and being composed of filamentous hyphae of a mycelial microorganism.

12. A process according to claim 11 wherein the mycelial spores are fungi of the genus Rhizopus or Mucor.

13. A process according to claim 11 wherein the agar beads are washed with sterile water prior to incubating.

14. A process according to claim 11 or claim 12 wherein dispersing the said mixture is accomplished by spraying.

15. A process according to claim 11 wherein the cooling in step (b) is carried out at a temperature ranging between about 45° to 80° C.

16. A process according to claim 15 wherein the medium solution is cooled to about 50° C.

17. A process according to claim 11 wherein the aqueous precipitation solution is the aqueous culture medium.

18. A process according to claim 11 wherein the droplets are dispersed by spraying into cool air.

19. A process according to claim 11 wherein the droplets are dispersed by spraying into cool water.

20. A spherical shaped mycelial pellet produced according to the process of claim 1.

21. A pellet according to claim 20 wherein said cellulose derivative is selected from the group consisting of cellulose acetate, cellulose triacetate and cellulose nitrate.

22. A spherical shaped mycelial pellet produced according to the process of claim 11.

23. A pellet according to claim 1 or claim 22 wherein said microorganism is a fungi of the genus Rhizopus, Mucor, Aspergillus, Pencillium or Trichoderma.

24. A pellet according to claim 20 or claim 22 having a core diameter ranging from about 0.1 mm to 1.0 cm and a layer thickness of about 1 mm to 5 mm.

25. A method for the biocatalytic conversion of organic compounds which comprises reacting said compounds in the presence of the mycelial pellet of claim 20 or claim 22.

26. A method according to claim 25 wherein a carbohydrate material is converted to alcohol and said microorganism is a fungi of the genus Rhizopus, Mucor, or mixtures thereof.

27. A method according to claim 25 wherein said conversion is carried out continuously in a column reactor containing said mycelial pellets.

28. A biocatalytic column reactor containing the mycelial pellet of claim 20 or claim 22.

* * * * *